(12) United States Patent
Carrasquillo

(10) Patent No.: US 6,342,038 B1
(45) Date of Patent: Jan. 29, 2002

(54) ELECTRONIC PULSE RATE COUNTER

(76) Inventor: Alberto Carrasquillo, 554 Summer St., Long Branch, NJ (US) 07740

(*) Notice: Subject to any disclaimer, the term of this patent is extended or adjusted under 35 U.S.C. 154(b) by 0 days.

(21) Appl. No.: 09/703,634

(22) Filed: Nov. 2, 2000

(51) Int. Cl.[7] ................................................. A61B 5/02
(52) U.S. Cl. ........................ 600/500; 600/527; 600/528
(58) Field of Search ............................... 600/481, 500, 600/527, 528, 586

(56) References Cited

U.S. PATENT DOCUMENTS 4,407,295 A * 10/1983 Steuer et al. ................ 600/483
6,210,344 B1 * 4/2001 Perin et al. .................. 600/528

* cited by examiner

Primary Examiner—Robert L. Nasser
Assistant Examiner—Patricia Mallari

(57) ABSTRACT

An electronic pulse rate counter for snapping onto the rubber tubing of, and interfacing with, a conventional stethoscope. The counter includes a housing for snapping onto the rubber tubing of the conventional stethoscope, a sensor that is operatively connected to the housing for interfacing with, and sensing pulses traveling through, the rubber tubing of the conventional stethoscope, a digital display that is visible through the housing and which electrically communicates with the sensor for displaying a rate of the pulses traveling through the rubber tubing of the conventional stethoscope sensed by the sensor, and circuitry that electrically communicates with both the sensor and the digital display for allowing the digital display to display the rate of the pulses traveling through the rubber tubing of the conventional stethoscope sensed by the sensor. The housing has an interior, a rear surface with a door that provides access to the interior of the housing, and a clip that is disposed on the door thereof, which provides a grip that facilitates removal and replacement of the door of the housing, and for snapping the housing onto the rubber tubing of the conventional stethoscope. The circuitry includes a battery interface for interfacing with a battery, which is disposed directly behind the door of the housing for facilitating access to the battery.

11 Claims, 1 Drawing Sheet

ELECTRONIC PULSE RATE COUNTER

BACKGROUND OF THE INVENTION

1. Field of the Invention

The present invention relates to an electronic pulse rate counter. More particularly, the present invention relates to an electronic pulse rate counter for snapping onto rubber tubing of, and interfacing with, a conventional stethoscope.

2. Description of the Prior Art

Medical personnel frequently require to know a patient's heart rate, and as a result thereof, measurement of the frequency of the human heartbeat is routinely undertaken during the course of physical examinations.

During such examinations, the physician uses a stethoscope to listen to the sounds of the heart and other areas of the patient's body. While listening to the heart, the physician measures the pulse rate by counting the number of pulses heard within a timed interval, during which time, the physician's attention is focused on a watch or other time measuring devices. This procedure is not only time consuming, but also liable to error, and does not provide heart rate readouts.

Numerous innovations for stethoscopes have been provided in the prior art that will be described. Even though these innovations may be suitable for the specific individual purposes to which they address, however, they differ from the present invention in that they not teach an electronic pulse rate counter for snapping onto rubber tubing of, and interfacing with, a conventional stethoscope.

FOR EXAMPLE, U.S. Pat. No. 4,377,727 to Schwalbach teaches an improved stethoscope having means for measuring the frequency of a series of pulses, such as human heart pulses, in the use of which such pulses are detected simultaneously with detection of a series of timed detectable reference impulses produced by a reference impulse producer having means for adjusting the frequency of the reference impulses produced thereby and also having readout means indicating the frequency of the reference impulses, wherefore upon adjustment of the frequency of the reference impulses as necessary to match that of said pulses, the frequency of said pulses is indicated on the readout means.

ANOTHER EXAMPLE, U.S. Pat. No. 4,618,986 to Hower teaches an electronic stethoscope having a palm sized electronic component case with operating switches provided on opposite sides of the case for ease of operation. The stethoscope includes a pickup head coupled to an electronic microphone by means of a flexible tubular acoustic member. A battery powered amplifier and filter circuit is provided within the component case and the amplified and filtered output of the microphone is coupled to a miniature speaker sealed within an airtight container within the case. A rotatable tubular member having radial apertures therein is coupled through the sealed container and out each side of the component case. A binaural headpiece is acoustically coupled to each end of the rotatable member and is thus free to rotate with respect to the case, allowing the stethoscope to fold for storage. In a preferred embodiment of the present invention, electronic timing means are provided for automatically removing electrical power from than amplifier circuit after a predetermined period of time and for generating an audible tone at preselected intervals for pulse rate measurement.

STILL ANOTHER EXAMPLE, U.S. Pat. No. 4,436,096 to Dyck et al. teaches a pulse/sound transducer for detecting electrical signals corresponding to heart sounds that are filtered in a narrow bandpass filter whose pass band is centered on a characteristic heart sound frequency of 33 Hz. The filter improves signal-to-noise ratio and enables the transducer to be used over a patient's clothing. The unfiltered signal is amplified and fed to binaural leads to provide the function of an electronic stethoscope. In addition, the filtered signal is converted into pulses in response to which a count corresponding to the detected heart rate is established in a counter and displayed as a digital heart rate indication.

YET ANOTHER EXAMPLE, U.S. Pat. No. 4,972,841 to Iguchi teaches a miniaturized electronic stethoscope designed to be used in conjunction with a standard sphygmomanometer in the measurement of blood pressure and pulse rate simultaneously in which a transducer converts the Korotkoff sounds into electrical signals. The electrical signals are amplified and fed to a counter in which the detected pulse rate per unit time is calculated and then the result is displayed as a digital pulse rate.

STILL YET ANOTHER EXAMPLE, U.S. Pat. No. 5,638,453 to McLaughlin teaches a transducer enhanced stethoscope including a head piece that has an ear piece at each end and is connected to bifurcated flexible tubing. The bifurcated tubing is integral a flexible short tube. Included is a pickup head that has a top face, a bottom face and a peripheral wall with a connector projecting therefrom. The top face has a pair of temperature sensors fixedly attached. Each temperature sensor is capable of measuring skin temperature for displaying on a top readout screen. The bottom face has a pulse sensor. The pulse sensor is capable of measuring blood flow rate for displaying on a bottom readout screen. A battery is sealed within the pickup head by a battery door that is accessible along the bottom face. Lastly, an elongated flexible tubing is coupled to the connector of the pickup head. The elongated tubing is capable of transmitting acoustical sound waves from the pickup head to the head piece.

It is apparent that numerous innovations for stethoscopes have been provided in the prior art that are adapted to be used. Furthermore, even though these innovations may be suitable for the specific individual purposes to which they address, however, they would not be suitable for the purposes of the present invention as heretofore described.

ACCORDINGLY, AN OBJECT of the present invention is to provide an electronic pulse rate counter for snapping onto rubber tubing of, and interfacing with, a conventional stethoscope that avoids the disadvantages of the prior art.

ANOTHER OBJECT of the present invention is to provide an electronic pulse rate counter for snapping onto rubber tubing of, and interfacing with, a conventional stethoscope that is simple and inexpensive to manufacture.

STILL ANOTHER OBJECT of the present invention is to provide an electronic pulse rate counter for snapping onto rubber tubing of, and interfacing with, a conventional stethoscope that is simple to use.

BRIEFLY STATED, YET ANOTHER OBJECT of the present invention is to provide an electronic pulse rate counter for snapping onto rubber tubing of, and interfacing with, a conventional stethoscope. The counter includes a housing for snapping onto the rubber tubing of the conventional stethoscope, a sensor that is operatively connected to the housing for interfacing with, and sensing pulses traveling through, the rubber tubing of the conventional stethoscope, a digital display that is visible through the housing and which electrically communicates with the senor for displaying a rate of the pulses traveling through the rubber tubing of the conventional stethoscope sensed by the sensor, and circuitry that electrically communicates with both the sensor and the digital display for allowing the digital display to display the rate of the pulses traveling through the rubber tubing of the conventional stethoscope sensed by the sensor. The housing has an interior, a rear surface with a door that provides access to the interior of the housing, and a clip that is disposed on the door thereof, and which provides a grip that facilitates removal and replacement of the door of the housing, and for snapping the housing onto the rubber tubing of the conventional stethoscope. The circuitry includes a battery interface for interfacing with a battery, and which is disposed directly behind the door of the housing for facilitating access to the battery.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described as follows.

Figure 1:
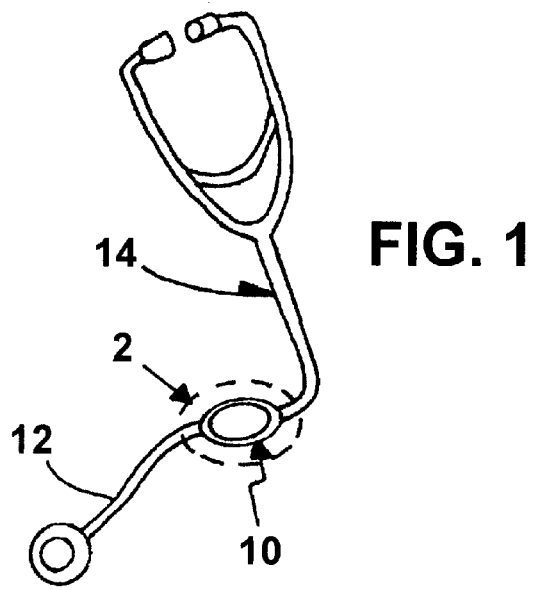
FIG. 1 is a diagrammatic perspective view of the present invention in use.

LIST OF REFERENCE NUMERALS UTILIZED IN THE DRAWING 10 electronic pulse rate counter of present invention for snapping onto rubber tubing of 12, and interfacing with, conventional stethoscope 14
12 rubber tubing of conventional stethoscope 14
14 conventional stethoscope
16 housing for snapping onto rubber tubing 12 of conventional stethoscope 14
18 sensor for interfacing with, and sensing pulses traveling through, rubber tubing 12 of conventional stethoscope 14
20 digital display for displaying rate of pulses traveling through rubber tubing 12 of conventional stethoscope 14 sensed by sensor 18
22 circuitry for allowing digital display 20 to display rate of pulses traveling through rubber tubing 12 of conventional stethoscope 14 sensed by sensor 18
24 front surface of housing 16 for facing ambient
26 rear surface of housing 16 for facing rubber tubing 12 of conventional stethoscope 14
28 interior of housing 16
30 perimeter of housing 16
32 door in rear surface 24 of housing 16
34 clip of housing 16 for snapping housing 16 onto rubber tubing 12 of conventional stethoscope 14
36 buttons of circuitry 22
38 battery interface of circuitry 22 for interfacing with battery (not shown)

DETAILED DESCRIPTION OF THE PREFERRED EMBODIMENT

Referring now to the figures, in which like numerals indicate like parts, and particularly to FIG. 1, which is a diagrammatic perspective view of the present invention in use, the electronic pulse rate counter of the present invention is shown generally at 10 for snapping onto rubber tubing 12 of, and interfacing with, a conventional stethoscope 14.

Figure 2:
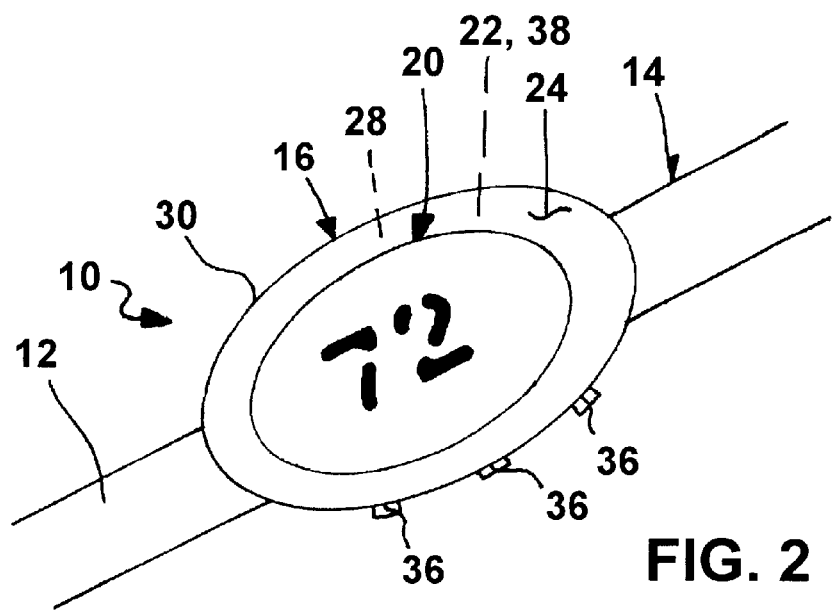
FIG. 2 is an enlarged diagrammatic perspective view of the area generally enclosed by the dotted curve identified by ARROW 2 in FIG. 1 of the present invention.
Figure 3:
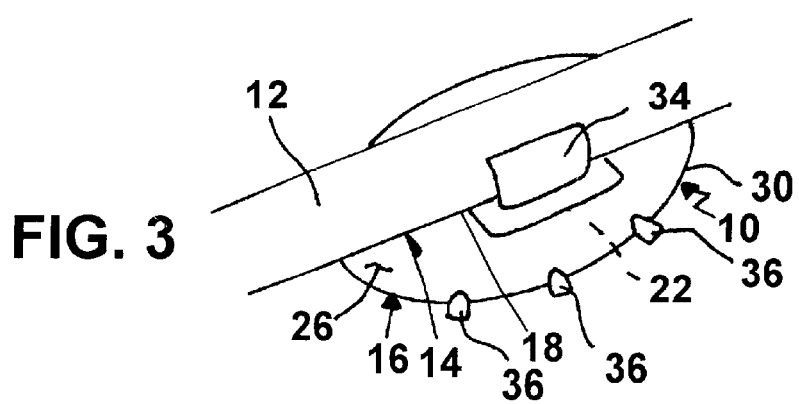
FIG. 3 is an enlarged diagrammatic perspective view taken generally in the direction of ARROW 3 in FIG. 2.

The configuration of the electronic pulse rate counter 10 of the present invention can best be seen in FIGS. 2 and 3, which are, respectively, an enlarged diagrammatic perspective view of the area generally enclosed by the dotted curve identified by ARROW 2 in FIG. 1 of the present invention, and an enlarged diagrammatic perspective view taken generally in the direction of ARROW 3 in FIG. 2, and as such, will be discussed with reference thereto.

The electronic pulse rate counter 10 comprises a housing 16 for snapping onto the rubber tubing 12 of the conventional stethoscope 14.

The electronic pulse rate counter 10 further comprises a sensor 18 that is operatively connected to the housing 16 for interfacing with, and sensing pulses traveling through, the rubber tubing 12 of the conventional stethoscope 14.

The electronic pulse rate counter 10 further comprises a digital display 20 that is visible through the housing 14 and electrically communicates with the sensor 18 for displaying a rate of the pulses traveling through the rubber tubing 12 of the conventional stethoscope 14 sensed by the sensor 18.

The electronic pulse rate counter 10 further comprises circuitry 22 that electrically communicates with both the sensor 18 and the digital display 20 for allowing the digital display 20 to display the rate of the pulses traveling through the rubber tubing 12 of the conventional stethoscope 14 sensed by the sensor 18.

The housing 16 is disk-shaped with rounded edges so as to have no sharp edges for at least one of cutting into, and damaging, the rubber tubing 12 of the conventional stethoscope 14 and injuring a user (not shown).

The housing 16 has a front surface 24 for facing the ambient, a rear surface 26 for facing the rubber tubing 12 of the conventional stethoscope 14, an interior 28, and a perimeter 30.

The rear surface 24 of the housing 16 has a door 32 that is circular-shaped, replaceable, and provides access to the interior 28 of the housing 16.

The housing 16 further has a clip 34 that is disposed on the door 32 thereof, and which provides a grip that facilitates removal and replacement of the door 32 thereof, and for snapping the housing 16 onto the rubber tubing 12 of the conventional stethoscope 14.

The clip 34 is springy, substantially U-shaped, and opens outwardly from the rear surface 26 of the housing 16 for receiving the rubber tubing 12 of the conventional stethoscope 14.

The sensor 18 is operatively disposed on the rear surface 26 of the housing 16 for contacting, and interfacing with, the rubber tubing 12 of the conventional stethoscope 14.

The digital display 20 is disposed in, and is visible through the front surface 24 of, the housing 16 for being easily discernable by the user (not shown) during use of the conventional stethoscope 14.

The circuitry 22 is disposed in the housing 16.

The circuitry 22 includes buttons 36 that are operatively connected to, and set, the circuitry 22, and which extend radially outwardly from the perimeter 30 of the housing 16 for easy access by the user (not shown).

The circuitry 22 further includes a battery interface 38 for interfacing with a battery (not shown), and which is disposed directly behind the door 32 of the housing 16 for facilitating access to the battery (not shown).

It will be understood that each of the elements described above, or two or more together, may also find a useful application in other types of constructions differing from the types described above.

While the invention has been illustrated and described as embodied in an electronic pulse rate counter for snapping onto rubber tubing of, and interfacing with, a conventional stethoscope, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An electronic pulse rate counter for snapping onto rubber tubing of, and interfacing with, a conventional stethoscope, comprising:
   a) a housing for snapping onto the rubber tubing of the conventional stethoscope;
   b) a sensor operatively connected to said housing for interfacing with, and sensing pulses traveling through, the rubber tubing of the conventional stethoscope;
   c) a digital display visible through said housing and electrically communicating with said sensor for displaying a rate of the pulses traveling through the rubber tubing of the conventional stethoscope sensed by said sensor; and
   d) circuitry electrically communicating with both said sensor and said digital display for allowing said digital display to display the rate of the pulses traveling through the rubber tubing of the conventional stethoscope sensed by said sensor.

2. The counter as defined in claim 1, wherein said housing is disk-shaped with rounded edges so as to have no sharp edges for at least one of cutting into, and damaging, the rubber tubing of the conventional stethoscope and injuring a user.

3. The counter as defined in claim 1, wherein said housing has:
   a) a front surface for facing the ambient;
   b) a rear surface for facing the rubber tubing of the conventional stethoscope;
   c) an interior; and
   d) a perimeter.

4. The counter as defined in claim 3, wherein said rear surface of said housing has a door that is circular-shaped, replaceable, and provides access to said interior of said housing.

5. The counter as defined in claim 4, wherein said housing further has a clip that is disposed on said door thereof, and which provides a grip that facilitates removal and replacement of said door thereof, and for snapping said housing onto the rubber tubing of the conventional stethoscope.

6. The counter as defined in claim 5, wherein said clip is springy, substantially U-shaped, and opens outwardly from said rear surface of said housing for receiving the rubber tubing of the conventional stethoscope.

7. The counter as defined in claim 3, wherein said sensor is operatively disposed on said rear surface of said housing for contacting, and interfacing with, the rubber tubing of the conventional stethoscope.

8. The counter as defined in claim 3, wherein said digital display is disposed in, and is visible through said front surface of, said housing for being easily discernable by the user during use of the conventional stethoscope.

9. The counter as defined in claim 1, wherein said circuitry is disposed in said housing.

10. The counter as defined in claim 3, wherein said circuitry includes buttons that are operatively connected to, and set, said circuitry, and which extend radially outwardly from said perimeter of said housing for easy access by the user.

11. The counter as defined in claim 4, wherein said circuitry includes a battery interface for interfacing with a battery, and which is disposed directly behind said door of said housing for facilitating access to the battery.

* * * * *